United States Patent [19]

Abell

[11] Patent Number: 5,398,687

[45] Date of Patent: Mar. 21, 1995

[54] METHODS FOR MEASURING MOTILITY WITHIN THE BILIARY TRACT AND INSTRUMENTATION USEFUL THEREFOR

[75] Inventor: Thomas L. Abell, Memphis, Tenn.

[73] Assignee: Wilson-Cook Medical Inc., Winston-Salem, N.C.

[21] Appl. No.: 885,156

[22] Filed: May 18, 1992

[51] Int. Cl.[6] .................................................. A61B 6/00
[52] U.S. Cl. .................................... 128/654; 128/656; 128/642; 128/780
[58] Field of Search ................................. 128/654–658, 128/642, 748, 780; 607/122

[56] References Cited

U.S. PATENT DOCUMENTS

| | | | |
|---|---|---|---|
| 3,825,015 | 7/1974 | Berkovits | 128/786 |
| 4,044,758 | 8/1977 | Patel | 604/125 |
| 4,063,548 | 12/1977 | Klatt et al. | 128/748 |
| 4,073,287 | 2/1978 | Bradley et al. | 128/642 |
| 4,718,423 | 1/1988 | Willis et al. | 128/786 |
| 4,734,094 | 3/1988 | Jacob et al. | 128/656 |
| 4,883,459 | 11/1989 | Calderon | 128/656 |
| 5,025,786 | 6/1991 | Siegel | 128/673 |
| 5,081,990 | 1/1992 | Deletis | 128/784 |
| 5,119,832 | 6/1992 | Xavier | 128/642 |
| 5,184,619 | 2/1993 | Austin | 128/748 |

*Primary Examiner*—Lee S. Cohen
*Assistant Examiner*—Brian L. Casler
*Attorney, Agent, or Firm*—Woodard, Emhardt, Naughton, Moriarty & McNett

[57] ABSTRACT

New devices and methods for detecting and diagnosing motility abnormalities within the pancreaticobiliary tree are disclosed. In the first device, a modified ERCP catheter with electrical activity sensing is positionable within the biliary tract, and operates to sense electrical activity during the ERCP procedure. Electrical activity is sensed by two circumferential leads formed by bands of silver, located near the distal tip of the catheter. The detection of electrical activity, in combination with the simultaneous radioscopic visualization of the biliary tract, provides a detailed motility profile for the physician without requiring the additional use of a perfusion catheter. A second device is also disclosed which detects motility within the biliary tract by the simultaneous sensing of electrical activity and surrounding fluid pressure. A biliary catheter has two circumferential silver leads and three perfusion lumens whose outlets are alternately spaced between the silver leads. When positioned within the biliary tract, this catheter yields valuable data correlating electrical activity and the corresponding occurrence of muscle activity. By the sequential detection of pressure changes at the proximal, medial, and distal perfusion outlets interspersed between the electrical activity leads, both the presence and direction of muscle activity are sensed in relation to the sensed electrical activity about the leads.

14 Claims, 4 Drawing Sheets

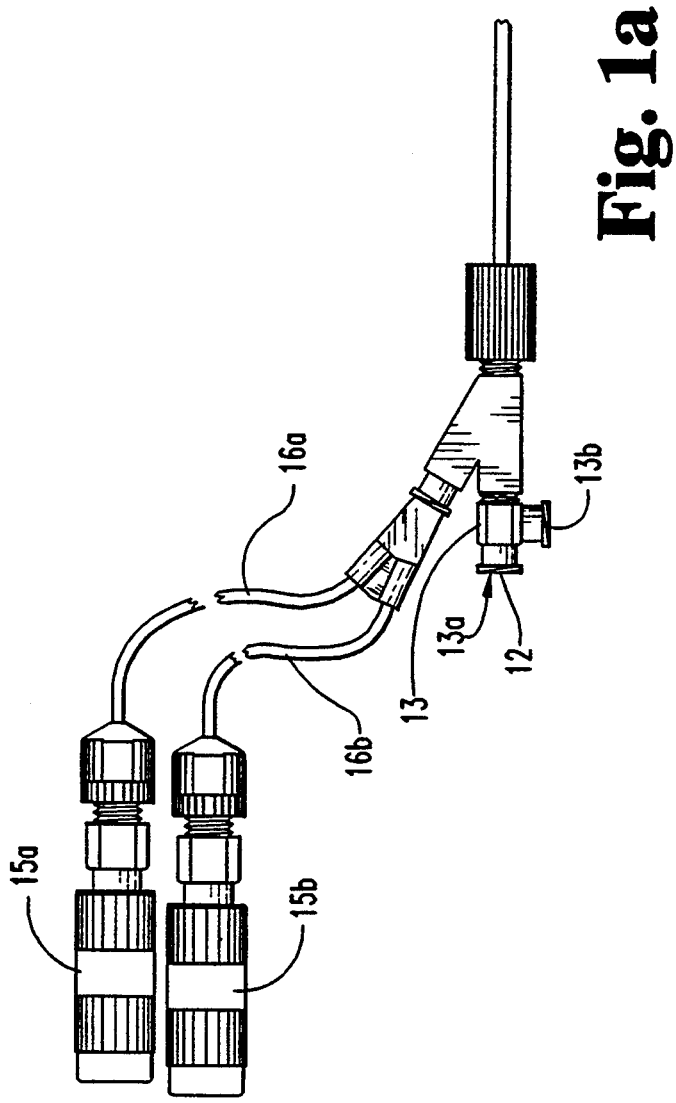
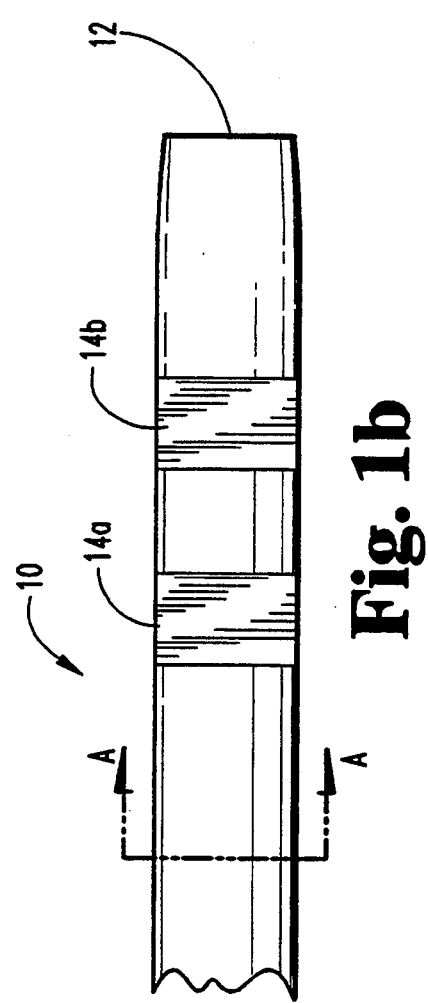
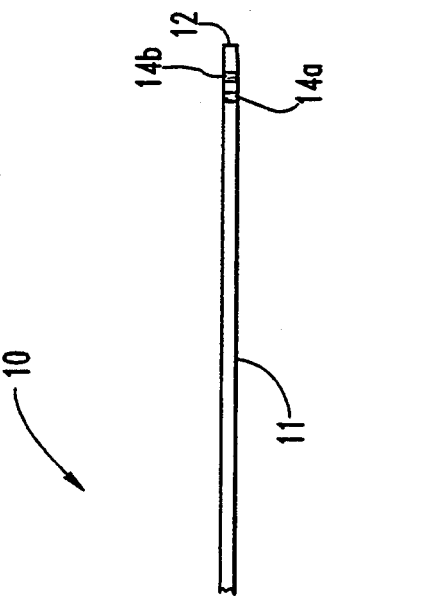
Fig. 1a
Fig. 1b
Fig. 1c

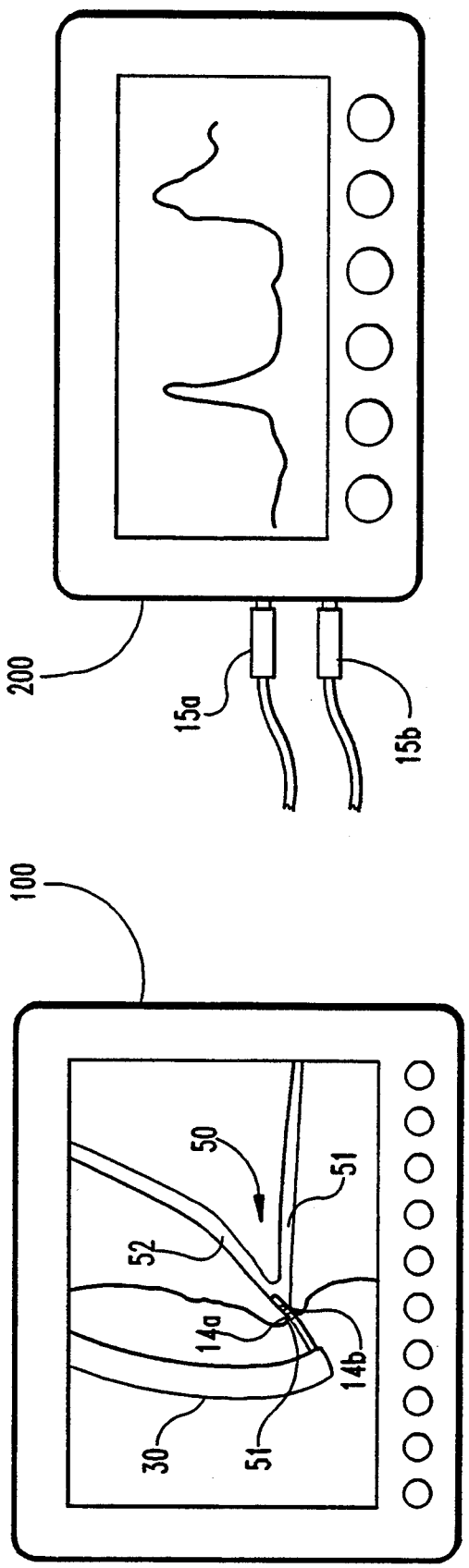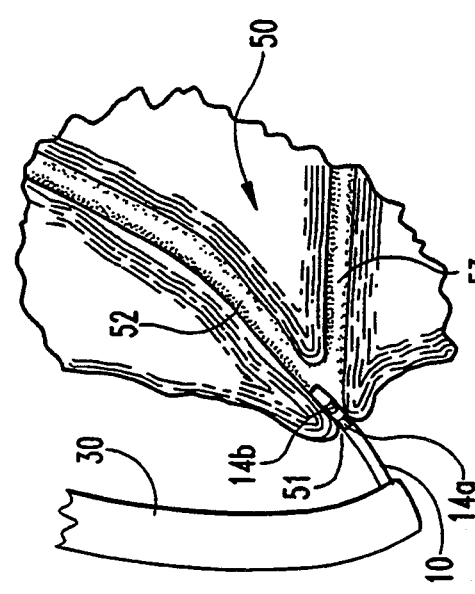

5,398,687

METHODS FOR MEASURING MOTILITY WITHIN THE BILIARY TRACT AND INSTRUMENTATION USEFUL THEREFOR

BACKGROUND OF THE INVENTION

1. Field of the Invention

The field of this invention relates to methods and devices for measuring motility within the biliary tract.

2. Description of the Prior Art

Prior to this invention, measurements of biliary tract anatomy and motility have generally been accomplished by means of radiologic and fluid pressure (manometric) measurements. Such measurements are commonly taken radiologically by means of a procedure called endoscopic retrograde cholangiopancreatography (ERCP). In an ERCP procedure, a portion of the pancreaticobiliary tree is cannulated and radiologically opaque contrast medium is injected into the biliary system. The flow of the injected contrast medium through the biliary system is then observed radiographically. In this way, abnormalities in motility within the biliary tract can be visually observed. Attendant with the ERCP procedure is the disadvantage that it requires the use of radiologically opaque materials within the body, and also involves exposing the patient to radiation in order to provide radiographic visualization.

Sometimes during an ERCP procedure, pressure measurements within the biliary tract are taken by means of a perfusion catheter. By this technique, a fluid, typically water, is supplied through lumens in a perfusion catheter, and pressure readings are taken which indicate the extent of pressure at the outlets of the catheter within tile biliary tract. An increase in sensed pressure is indicative of a muscle contraction in the area of the outlet. Due to tile constant flow of fluids which are required to be perfused into the biliary system, inflammation of the biliary or pancreatic duct can potentially result from the use of this technique.

These above techniques are also limited in that they only provide to the attending physician information as to the actual physical motility of the biliary tract, without providing reliable information as to the underlying cause of the detected motility or lack thereof. What is needed is a new device and technique for measuring motility within the biliary tract which is both safer to the patient and provides more helpful diagnostic information to the attending physician.

SUMMARY OF THE INVENTION

Generally speaking, the present invention provides a new and unique approach to the detection and diagnosis of motility abnormalities within the pancreaticobiliary tree. This new approach is performed with devices which simultaneously sense electrical activity during ERCP and/or perfusion procedures, and which thereby provide valuable additional diagnostic information to the doctor with techniques which are both safer and less invasive to the patient.

Two devices are disclosed. In the first device, a modified ERCP catheter with electrical activity sensing is positionable within the biliary tract, and operates to sense electrical activity during the ERCP procedure. Electrical activity is sensed by two circumferential leads formed by bands of silver, located near the distal tip of the catheter. The detection of electrical activity, in combination with the simultaneous radioscopic visualization of the biliary tract, provides a detailed motility profile for the physician without requiring the additional use of a perfusion catheter.

A second device is also disclosed which detects motility within the biliary tract by the simultaneous sensing of electrical activity and surrounding fluid pressure. A biliary catheter has two circumferential leads formed by bands of silver, and three perfusion lumens, whose outlets are alternately spaced between the silver leads. When positioned within the biliary tract, this catheter yields valuable data correlating electrical activity and the corresponding occurrence of muscle activity. By the sequential detection of pressure changes at the proximal, medial, and distal perfusion outlets interspersed between the electrical activity leads, both the presence and direction of muscle activity are sensed in relation to the sensed electrical activity about the leads. This catheter may be used in lieu of an ERCP procedure or in conjunction therewith.

BRIEF DESCRIPTION OF THE DRAWINGS

FIGS. 1a–c are views of an ERCP/electrical activity sensing catheter according to the present invention. FIG. 1a is a segmented side elevation view of the catheter. FIG. 1b is an enlarged view of the distal end portion of the catheter of FIG. 1a. FIG. 1c is a crossectional view of the catheter of FIGS. 1a–b, sectioned along lines A—A in FIG. 1b.

FIG. 2a is a segmented side elevation view of the catheter. FIG. 2b is an enlarged view of the distal end portion of the catheter of FIG. 2a. FIG. 2c is a crossectional view of the catheter of FIGS. 2a–b, sectioned along lines B—B in FIG. 1b.

FIGS. 3a–c illustrate the process of electrical activity sensing during an ERCP procedure, using the ERCP/electrical sensing catheter of FIGS. 1a–c. FIG. 3a shows the catheter positioned within the biliary tract for detection of motility through electrical sensing during an ERCP procedure. FIG. 3b shows the radioscopic visualization of the ERCP procedure being conducted. FIG. 3c illustrates the graphical output of sensed electrical activity during the procedure.

FIG. 4a shows the catheter positioned within the biliary tract for combined detection of motility through electrical and pressure sensing. FIG. 4b shows the graphical output of sensed electrical and corresponding muscular activity during the procedure.

DESCRIPTION OF THE PREFERRED EMBODIMENT

Figure 2A:
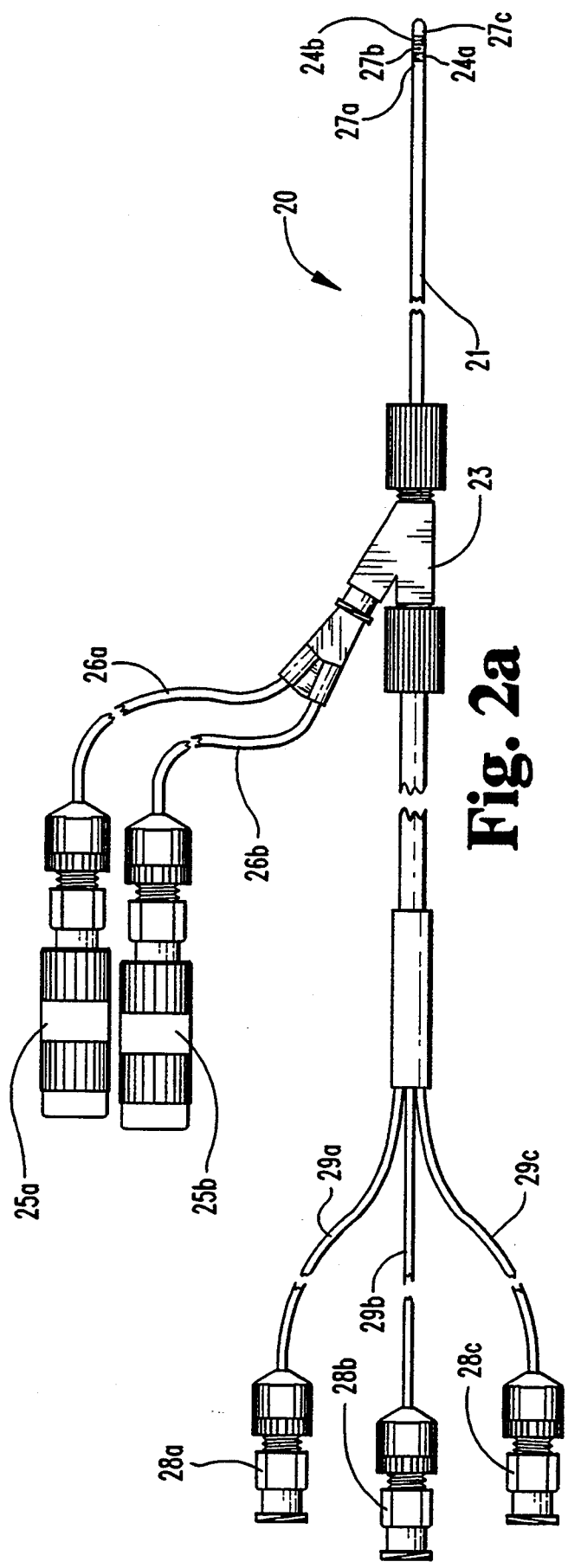
FIGS. 2a–c are views of an electrical/mechanical activity catheter for sensing biliary motility according to the present invention.

For the purposes of promoting an understanding of tire principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings, FIG. 1a is a segmented side elevation view of an ERCP/electrical activity sensing catheter 10 according to the present invention. Catheter 10 is constructed for endoscopic insertion into the biliary tract of a patient, where it functions to perform an ERCP procedure and to simultaneously detect the occurrence of electrical activity within the biliary tract while the procedure is being undertaken. For this purpose, elongate catheter body portion 11 is made of material which is flexible and biocompatible (Teflon, PVC, or other suitable material) and is sized (200 cm. in length) for advancement through a duodenal endoscope and into the biliary tract through the Sphincter of Oddi. Catheter 10 defines a lumen 12 therethrough which provides access into the biliary tract. At the proximal end of catheter 10 is luer lock fitting 13, which provides access ports 13a for receiving a wire guide through lumen 12, and 13b for the injection of contrast medium.

Near the distal end of catheter 10 are located two circumferential leads 14a–b which are formed by bands of silver. Leads 14a–b are each approximately 3 mm. in width and are distally spaced from each other about 3 mm. The more distal band 14b of the two is approximately 6 mm. from the tip of the catheter. FIG. 1b is an enlarged view of the distal end portion of the catheter of FIG. 1a. By providing for the detection of electrical activity while radioscopic visualization of the biliary tract is simultaneously being performed, leads 14a–b help to provide a detailed motility profile for the attending physician, and can serve as an aid in not only detecting the occurrence of motility abnormalities but also diagnosing the potential underlying causes thereof.

The above dimensions of width and separation of leads 14a–b are given for illustrative purposes to show a functional configuration that will detect electrical activity within biliary structures. Variations in individual and overall dimension that will accommodate the intended purpose are contemplated as within the scope of the present invention. In this regard, a ratio between the individual band width to the overall proximal to distal length of the combined leads of between 20–40% is considered sufficient to provide a good electrical signal output. Also, since signals are to be presented from structures as small as 1–2 cm. in length, the overall length should be sized to accommodate these dimensions, and preferably should be no more than about 10 mm. The specific distance from distal lead 14b to the tip of catheter 10 is also given as illustrative and may also be varied to accommodate individual preference. A distance within the range of 4–8 mm. is generally considered suitable for my personally preferred use.

At the proximal end of catheter 10 are located two electrical plugs 15a and 15b which are electrically connected to leads 14a–b respectively through wires 16a–b. FIG. 1c is a crossectional view of catheter 10, sectioned along lines A—A in FIG. 1b, and shows the positioning of wires 16a–b within lumen 12. Wires 16a–b, are insulated and sized within lumen 12 so that they do not interfere with either the advancement of a wire guide through lumen 12 or the injection of constract medium therethrough.

Figure 2C:
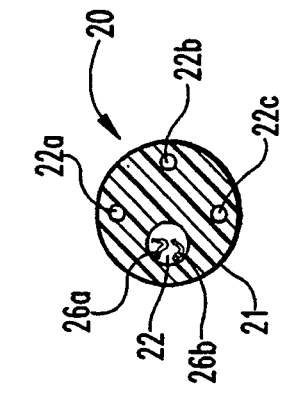
Figure 2B:
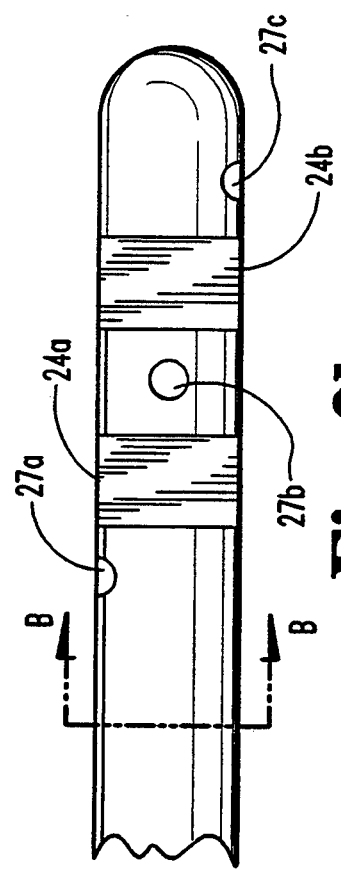

FIGS. 2a–c are views of an electrical/mechanical activity catheter 20 for sensing biliary motility according to the present invention. FIG. 2a is a segmented side elevation view of catheter 20. As with catheter 10, catheter 20 is also constructed for endoscopic insertion into the biliary tract of a patient, where it functions to simultaneously detect the occurrence of electrical activity and fluid pressure levels within the biliary tract. Accordingly, elongate catheter body portion 21 is made of material which is flexible and biocompatible (Teflon, PVC, or other suitable material) and is sized (200 cm. in length) for advancement through a duodenal endoscope and into the biliary tract through the Sphincter of Oddi. Near the distal end of catheter 20 are located two circumferential leads 24a–b which are formed by bands of silver. Leads 24a–b are each approximately 3 mm. in width and are distally spaced from each other about 3 mm. The more distal band 24b of the two is approximately 4 mm. from the tip of the catheter. At the proximal end of catheter 20 are located two electrical plugs 25a and 25b which are electrically connected to leads 24a–b respectively through wires 26a–b.

Manometric readings can be taken with catheter 20 through the use of perfusion lumens 22a–c which lead to outlets 27a–c near the distal end of catheter 20. Distal outlets 27a–c are interspersed between leads 24a–b. Proximally, lumens 22a–c are connected to tubes 29a–c which, in turn, connect to perfusion pods 28a–c respectively. FIG. 2c is a crossectional view of catheter 20, sectioned along lines B—B in FIG. 2b, and shows wires 26a–b positioned within lumen 22, and perfusion lumens 22a–c respectively.

By providing for the detection of electrical activity while simultaneously taking pressure readings at the same location within the biliary tract, catheter 20 helps to provide a detailed motility profile. When positioned within the biliary tract, catheter 20 yields valuable data correlating electrical activity and the corresponding occurrence of muscle activity. By the sequential detection of pressure changes at proximal 27a, middle 27b, and distal 27c perfusion outlets interspersed between electrical activity leads 24a and 24b, both the presence and direction of muscle activity are sensed in relation to the sensed electrical activity.

FIGS. 3a–c illustrate the process of electrical activity sensing during an ERCP procedure, using ERCP/electrical sensing catheter 10 of FIGS. 1a–c. FIG. 3a shows catheter 10 advanced through duodenal endoscope 30 and the Sphincter of Oddi 51, and positioned within biliary tract 50 for detection of motility through electrical sensing during an ERCP procedure. FIG. 3a shows catheter 10 positioned with leads 14a–b located at the Sphincter of Oddi 51. Alternate locations at which leads 14a–b can be positioned to detect electrical activity data include the common bile duct 52 and the pancreatic duct 53.

FIG. 3b illustrates radioscopic visualization by means of radioscopy equipment 100 of the ERCP procedure being conducted in FIG. 3a. In FIG. 3b, biliary tract 50 is visualized by the injection of contrast medium of high radioscopic reflectivity through catheter 10 and into biliary tract 50. In FIG. 3b, it is also seen that the relative position of catheter 10 can be detected because of the high radioscopic reflectivity of leads 14a–b. Because leads 14a–b serve the dual purpose of electrical activity sensing and radioscopic visibility, leads 14a–b replace the need to separately apply radioscopically reflective markings on catheter 10.

FIG. 3c illustrates the graphical output of sensed electrical activity during the procedure by means of electrical equipment 200. In FIG. 3c, it is seen that electrical plugs 15a–b from catheter 10 have been inserted into inputs of electrical equipment 200, and that the electrical information being received thereby has been analyzed and graphically outputted. By reviewing and analyzing the combined information received from both radioscopic equipment 100 and electrical equipment 200, a physician can detect not only the existence of motility abnormalities, but can isolated the cause of such abnormalities as well.

Figure 4B:
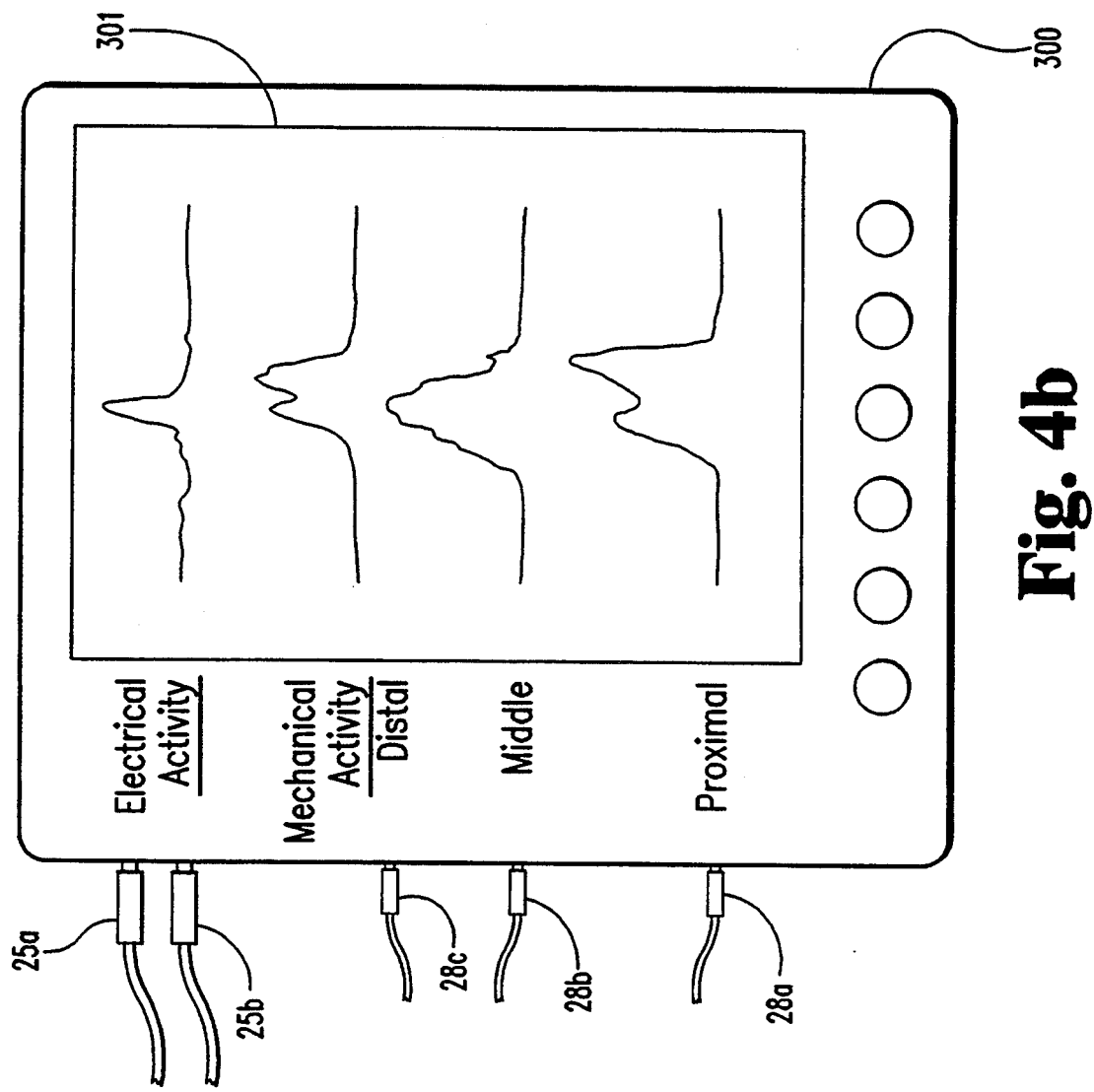
FIGS. 4a–b illustrate the process of using an electrical/mechanical activity catheter of FIGS. 2a–c for sensing biliary motility.
Figure 4A:
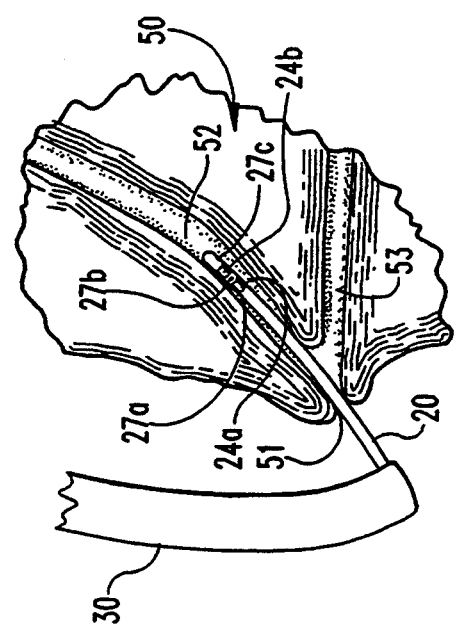

FIGS. 4a–b illustrate the process of using electrical/mechanical activity catheter 20 of FIGS. 2a–c for sensing biliary motility. FIG. 4a shows catheter 20 advanced through duodenal endoscope 30 and the Sphincter of Oddi 51, and positioned within biliary tract 50 for detection of motility through combined electrical/mechanical sensing. FIG. 3a shows catheter 20 positioned with leads 14a–b and perfusion outlets 27a–c located at the common bile duct 52. Alternate locations at which leads 14a–b and perfusion outlets can be positioned to detect electrical/mechanical activity data include the Sphincter of Oddi 51 and the pancreatic duct 53.

FIG. 4b shows the graphical output of sensed electrical/mechanical activity during the procedure of FIG. 4a by means of electrical/mechanical detection equipment 300. In FIG. 4b, it is seen that electrical plugs 25a–b and perfusion ports 28a–c are plugged into inputs in equipment 300, and that the electrical and mechanical information being received thereby is being analyzed by equipment 300 and graphically outputted thereby on graph 301. By the sequential detection of both electrical activity at leads 24a–b and pressure changes at the proximal, medial, and distal perfusion outlets 27a–c interspersed between leads 24a–b, both the presence and direction of muscle activity are sensed in relation to tile sensed electrical activity about leads 24a–b. In this way, a physician can isolated tile cause of motility abnormalities as arising from electrical and or muscular causes, and prescribe appropriate treatment as indicated.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention am desired to be protected.

What is claimed is:

1. A method for measuring motility within a biliary tract, said method comprising the steps of:
    inserting an ERCP/electrical activity sensing catheter having a distal tip through an endoscope and into the biliary tract through the Sphincter of Oddi, said catheter defining a lumen through which radioscopically reflective contrast medium may be injected therethrough into the biliary tract, said catheter further including two circumferential electrical leads formed about said catheter near its distal tip and positionable within the biliary tract;
    positioning said catheter with said leads positioned within the biliary tract;
    injecting radioscopically reflective contrast medium through said catheter and into the biliary tract; and
    observing the operation of the biliary tract through radioscopic visualization equipment while simultaneously detecting electrical activity sensed within the biliary tract by said electrical leads.

2. The method for measuring motility within the biliary tract of claim 1 in which said leads are positioned within the Sphincter of Oddi.

3. The method for measuring motility within the biliary tract of claim 1 in which said leads are positioned within the common bile duct.

4. The method for measuring motility within the biliary tract of claim 1 in which said leads are positioned within the pancreatic duct.

5. A method for measuring motility within a biliary tract, said method comprising the steps of:
    inserting an electrical/mechanical activity sensing catheter having a distal tip through an endoscope and into the biliary tract through the Sphincter of Oddi, said catheter including two circumferential electrical leads formed about said catheter near its distal tip and positionable within the biliary tract, and further including pressure sensing means for enabling the sensing of fluid pressure in the vicinity of said leads;
    positioning said catheter with said leads positioned within the biliary tract; and
    observing biliary tract motility by observing fluid pressure measurements about said electrical leads while simultaneously detecting electrical activity sensed within the biliary tract by said electrical leads.

6. The method for measuring motility within the biliary tract of claim 5 in which said leads are positioned within the Sphincter of Oddi.

7. The method for measuring motility within the biliary tract of claim 5 in which said leads are positioned within the common bile duct.

8. The method for measuring motility within the biliary tract of claim 5 in which said leads are positioned within the pancreatic duct.

9. An ERCP/electrical activity sensing catheter for measuring motility within a biliary tract, said catheter having a distal end which is positionable within the biliary tract and a proximal end opposite thereto and comprising:
    an elongate catheter body portion made of material which is flexible and biocompatible and sized for advancement through a duodenal endoscope and into the biliary tract through the Sphincter of Oddi, said elongate catheter body portion defining a lumen through which radioscopically reflective contrast medium may be injected therethrough into the biliary tract; and
    two circumferential electrical leads each having a proximal and distal end are formed about said catheter body portion near the distal end of said catheter and positionable within the biliary tract, said leads being electrically connected to external electrical plugs located at the proximal end of said catheter;
    pressure sensing means for enabling the sensing of fluid pressure in the vicinity of said leads, said pressure sensing means including at least one distal outlet located in the vicinity of said electrical leads and a perfusion lumen fluidly connecting said distal outlet with a perfusion port located at the proximal end of said catheter;
    wherein the operation of the biliary tract through radioscopic visualization equipment may thus be observed simultaneously with the detection of electrical activity sensed within the biliary tract by said electrical leads and pressure sensed within the biliary tract through said pressure sensing means; and
    wherein said pressure sensing means includes three distal outlets alternatively spaced between said electrical leads, and three corresponding perfusion lumens and perfusion ports, and where each of said perfusion lumens fluidly connects one of said three distal outlets with one of said three perfusion ports.

10. The ERCP/electrical activity sensing catheter for measuring motility within the biliary tract of claim 9 in which said circumferential leads are made of bands of silver.

11. The ERCP/electrical activity sensing catheter for measuring motility within the biliary tract of claim 9 in which the overall length from the proximal end of a more proximal of said leads along said elongate catheter body portion of said catheter to the distal end of a distal of said leads along said elongate catheter body portion of said catheter is no more than about 1 cm.

12. An electrical/mechanical activity sensing catheter for measuring motility within a biliary tract, said catheter comprising:

an elongate catheter body portion having a distal tip and made of material which is flexible and biocompatible and sized for advancement through a duodenal endoscope and into the biliary tract through the Sphincter of Oddi;

two circumferential electrical leads each having a proximal and distal end are formed about said catheter body portion near its distal tip and positionable within the biliary tract, said leads being electrically connected to external electrical plugs located at a proximal end of said catheter; and pressure sensing means for enabling the sensing of fluid pressure in the vicinity of said leads, said pressure sensing means including at least one distal outlet located in the vicinity of said electrical leads and a perfusion lumen fluidly connecting said distal outlet with a perfusion port located at the proximal end of said catheter;

wherein biliary tract motility may be observed by observing fluid pressure measurements about said electrical leads simultaneously with the detection of electrical activity sensed by said electrical leads; and wherein said pressure sensing means for enabling the sensing of fluid pressure in the vicinity of said leads includes three distal outlets alternatively spaced between said electrical leads, and three corresponding perfusion lumens and perfusion ports, and where each of said perfusion lumens fluidly connects one of said three distal outlets with one of said three perfusion ports.

13. The electrical/mechanical activity sensing catheter for measuring motility within the biliary tract of claim 12 in which said circumferential leads are made of bands of silver.

14. The electrical/mechanical activity sensing catheter for measuring motility within the biliary tract of claim 12 in which the overall length from the proximal end of a more proximal of said leads to the distal end of a more distal of said leads along said elongate catheter body portion of said catheter is no more than about 1 cm.

* * * * *